United States Patent [19]

Saito et al.

[11] 4,317,769
[45] Mar. 2, 1982

[54] FLAME RETARDANTS

[75] Inventors: Toranosuke Saito, Ibaragi; Hiroyuki Ohishi, Moriyama, both of Japan

[73] Assignee: Sanko Kaihatsu Kagaku Kenkyusho, Osaka, Japan

[21] Appl. No.: 131,722

[22] Filed: Mar. 19, 1980

[30] Foreign Application Priority Data

Mar. 19, 1979 [JP] Japan .................................. 54-31162
Jan. 25, 1980 [JP] Japan .................................. 55-6906

[51] Int. Cl.³ .......................... C07F 9/38; C08K 5/53
[52] U.S. Cl. ................................... 524/117; 252/609; 260/936; 528/176; 524/606; 524/611; 524/605
[58] Field of Search .................. 260/45.7 PT, 45.8 R, 260/936, 45.9 KA; 252/609; 528/176

[56] References Cited

U.S. PATENT DOCUMENTS

| | | | |
|---|---|---|---|
| 1,684,738 | 9/1928 | Marschalk | 260/936 |
| 3,216,970 | 11/1965 | Conix | 528/176 |
| 3,535,300 | 10/1970 | Gable | 260/45.8 SN |
| 3,557,053 | 1/1971 | Miller | 260/45.7 P |
| 3,702,878 | 11/1972 | Saito | 260/45.8 R |
| 4,086,206 | 4/1978 | Saito et al. | 260/45.8 R |
| 4,113,795 | 9/1978 | Izawa et al. | 260/45.8 R |
| 4,127,590 | 11/1978 | Endo et al. | 260/936 |
| 4,198,492 | 4/1980 | Izawa et al. | 260/45.8 R |
| 4,280,951 | 7/1981 | Saito et al. | 260/45.8 R |

OTHER PUBLICATIONS

Hilado, Flammability Handbook for Plastics, 1969, pp. 82–86.

*Primary Examiner*—John Kight, III
*Assistant Examiner*—R. A. White
*Attorney, Agent, or Firm*—Sughrue, Mion, Zinn, Macpeak and Seas

[57] ABSTRACT

Alkali metal salts or/and alkaline earth metal salts of cyclic phosphorus compounds expressed by the general formula

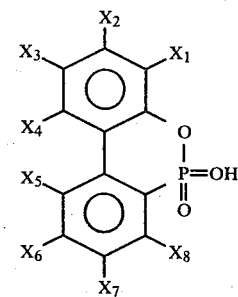

(wherein $X_1$ to $X_8$ each represent hydrogen, halogen, cyano group, acyl group, alkyl group, halogen-substituted alkyl group, aryl group, halogen-substituted aryl group or aralkyl group) are provided. These metal salts impart a specific flame retardancy to organic high molecular weight compounds prepared from alkylidenebisphenols as a raw material, without lowering the characteristic properties of substrates.

7 Claims, No Drawings

FLAME RETARDANTS

BACKGROUND OF THE INVENTION

This invention relates to novel flame retardants and more particularly it relates to flame retardants comprising alkali metal salts or (and) alkaline earth metal salts of specified phosphorus compounds.

Organic high molecular weight materials are usually easily combustible and it has recently been socially required to make these materials flame retardant. Thus, many flame retardants or flame retardant techniques have already been proposed or practically employed. However, when organic high molecular weight materials are made flame retardant by the use of flame retardants, it is usually necessary to add them in an amount of several % to ten and several %, hence there has been a draw back that physical or chemical characteristic properties intrinsic of organic high molecular weight materials as substrate are more or less harmed. On the other hand, among elements constituting flame retardants, halogens, phosphorus, antimony, nitrogen, etc. have heretofore been regarded as useful, but according to a series of recent patents, it has been found that an extremely small amount of alkali metal or alkaline earth metal compounds added to aromatic polycarbonate resins imparts a satisfactory, specific flame retardancy (see U.S. Pat. Nos. 3,775,367; 3,909,490; 3,917,559; 3,919,167; 3,926,908; 3,931,100; 3,933,734; 3,940,366; 3,948,851; 3,951,910; 3,953,396; 3,953,399; 3,978,024; 4,001,175; 4,007,155; 4,028,297; 4,032,506; 4,033,930; 4,039,509; and 4,064,101). However, the flame retardants disclosed in these patents also have two serious drawbacks. The first drawback is that since the compatibility of the flame retardants with substrates is inferior, the resulting resin compositions rendered flame retardant are generally opaque. In order to overcome such a drawback, there has been made an attempt to have the resulting compositions retain transparency although they are heterogeneous, by selecting flame retardants exhibiting the same refractive index as those of substrates (see U.S. Pat. Nos. 4,001,175; 4,007,155; and 4,039,509). Another drawback is that flame retardants are thermally unstable and have a tendency to be decomposed at high processing temperatures of the resulting resin compositions, and as a result, the molecular weights of substrates are reduced by the resulting decomposition products, resulting in a tendency to degrade characteristic properties such as impact-resistance.

SUMMARY OF THE INVENTION

Accordingly an object of this invention is to provide a flame retardant exhibiting a flame retardancy when added to high molecular weight materials as substrate in an extremely small amount; having a superior compatibility thereof with the substrate; and also having a high thermal stability.

Another object of this invention is to provide a resin composition having a good transparency and rendered highly flame retardant without lowering various characteristic properties such as high-impact properties intrinsic of substrates.

In accordance with this invention, there are provided a flame retardant comprising alkali metal salts or/and alkaline earth metal salts of cyclic phosphorus compounds expressed by the general formula (I)

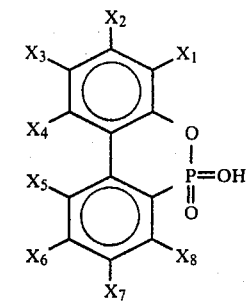

(wherein $X_1$ to $X_8$ each represent hydrogen, halogen, cyano group, acyl group, alkyl group, halogen-substituted alkyl group, aryl group, halogen-substituted aryl group or aralkyl group), and a composite flame retardant of the aforesaid flame retardant with an organic halogen compound or compounds.

DETAILED DESCRIPTION OF THE INVENTION

As has already been said, alkali metal or alkaline earth metal compounds exhibit a flame retardancy upon specified organic high molecular weight materials in an extremely small amount of the compounds. This is indeed specific and has been difficult to understand. In such a situation, however, certain findings suggesting a more fundamental function of alkali metals or alkaline earth metals in the flame retardancy of these metals, have been obtained through a number of researches and experiments. Necessary findings among the above-mentioned will be described for better understanding of this invention.

It is known that alkali metal or alkaline earth metal compounds exhibiting basic property such as oxides, hydroxides, carbonates, sulfides, alkoholates, phenolates, mercaptides or the like of these metals catalytically function upon alkylidenebisphenols when heated, to cause an endothermic decomposition reaction as shown by the following equation:

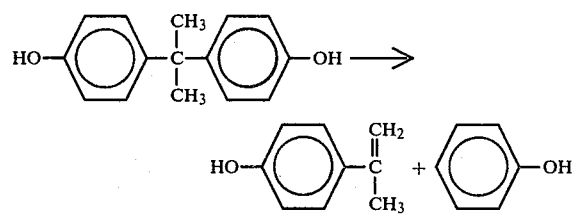

This decomposition reaction applies also to organic high molecular weight compounds composed of alkylidenebisphenols as in the case of aromatic polycarbonate resins, and a notable reduction in the molecular weight accompanying the decomposition reaction at the time of being heated is observed even in the presence of an extremely small amount of basic compounds. Whereas, in the case of organic high molecular weight compounds prepared for trial in a model manner from bifunctional phenols which are difficult to cause the above-mentioned endothermic decomposition reaction, such as 4,4'-methylenebisphenol, 4,4'-dioxydiphenyl, 4,4'-dioxydiphenyl ether, 4,4'-dioxydiphenyl sulfone or the like, almost no reduction in the molecular weight thereof due to heating is observed in the presence of a small amount of basic compounds. Further, in the case of aromatic polycarbonate resins, when they are mixed and heated together with alkali metal or alkaline earth metal compounds, notable reduction in the molecular weight occurs as mentioned above, to make it difficult to prepare a test piece by which flame retardancy can be evaluated, but if the both are mixed together in the presence of a solvent such as dioxane, methylene chloride or the like, at a low temperature, followed by drying, then a test piece by which flame retardancy can be evaluated is obtained. According to this, it is found that any of alkali metal or alkaline earth metal compounds exhibiting basic property exhibit a specific flame retardancy. On the contrary, any of alkali metal or alkaline earth metal compounds exhibit no specific flame retardancy with the above-mentioned organic high molecular weight compounds prepared for trial in a model manner from bifunctional phenols which do not cause any endothermic decomposition reaction. It can be presumed in view of these facts that the specific flame retardancy of the alkali metal or alkaline earth metal compounds be related to the above-mentioned endothermic decomposition reaction. However, practicable flame retardants are neutral and difficult to cause the endothermic decomposition reaction at least at temperatures at the time of molding processing; hence it should be presumed in order to explain the above-mentioned relationship that the neutral alkali metal or alkaline earth metal compounds might not be transformed into compounds exhibiting basic property, until they reach high temperatures at the time of combustion. This presumption is very important for the present invention. The fact that whether the transformation is difficult or easy is a factor determining the character of flame-retardants, and the justification of the presumption will be understood from the following description of the present invention.

In the flame retardants comprising alkali metal or alkaline earth metal salts of cyclic phosphorus compounds expressed by the above-mentioned general formula (I), $X_1$ to $X_8$ have a very great influence upon the flame retardancy and the compatibility with substrate. Among $X_1$ to $X_8$, the presence of electron-attractive groups i.e. halogen, cyano group, acyl group, halogen-substituted alkyl group, aryl group or halogen-substituted aryl group, increases the flame retardancy. Further, the extent of increase in the flame retardancy also varies depending on the intensity of electron-attractiveness, the number or the position of substitution of the electron-attractive groups. Namely, in the case of halogen, the extent to which the retardancy is increased is in the order of fluorine, chlorine and bromine, and as for the position of $X_1$ to $X_8$, contribution of the positions of even numbers thereof to the retardancy to be imparted by the election-attractive groups is greater than that of the positions of odd numbers thereof. The extent of the retardancy imparted by the election-attractive groups accords with the effectiveness of reducing the election density of $P=O$ in the general formula (I). The fact that the lower the electron density of oxygen, the easier the splitting-off of oxygen, as in the case of other oxygen acids, will be easily understood in view of the fact that the bonding of $P=O$ (which should be correctly designated as $P\Delta O$) comes into existence due to electron donation from phosphorus atom to oxygen atom. Further it is apparent that when the alkali metal or alkaline earth metal salts of the general formula (I) lose oxygen, basic property is exhibited. The above-mentioned presumption may be induced from these facts. The donation and acceptance of oxygen must be carried out in the form of oxidation and reduction in the resin composition, but what is oxidized is unknown. The temperature at which this oxidation and reduction begin to occur, not to mention the easiness with which the oxidation and reduction occur, depend on the easiness with which the oxygen in the $P=O$ bond splits off. If oxygen is extremely difficult to be split off and hence oxidation and reduction do not occur or only slowly occur even at high temperatures at the time of combustion, then no specific flame retardancy is exhibited. For example, in the case of a potassium salt of the general formula (I) wherein $X_1$ and $X_3$ are both t-butyl group and $X_2$, $X_4$, $X_5$, $X_6$, $X_7$ and $X_8$ are all hydrogen, the specific flame retardancy is relatively small.

On the other hand, if oxygen is too easily split off and the oxidation and reduction begin to occur already at temperatures at the time of molding processing, then the decomposition of substrate is promoted at the time of molding processing to lower the impact resistance of the substrate. For example, in the case of a potassium salt of the general formula (I) wherein $X_1$ to $X_8$ are all chlorine, an extremely high flame retardancy is exhibited, but if this salt is present in aromatic polycarbonate resins in an amount of 1% by weight or more, there is observed a tendency that the impact resistance is lowered at molding temperatures of 340° C. or higher.

Further, the substituents of $X_1$ to $X_8$ have a great influence upon the compatibility of substrates with the flame retardants. In the case of alkali metal or alkaline earth metal salts of the general formula (I) wherein $X_1$ to $X_8$ are all hydrogen, only the worst compatibility is exhibited among those of the flame retardants of the present invention. All other substituents improve the compatibility. Particularly, alkyl group, aryl group and aralkyl group have an effectiveness of imparting a superior compability. An ideal structure to be possessed by the general formula (I) can be selected taking such effects of substituents into account.

Since the cyclic phosphorus compounds expressed by the general formula (I) are complicated in the nomenclature, they are expressed in terms of the following phenanthrene ring in the present invention so that the description may be made convenient:

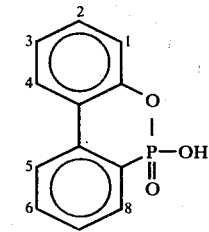

(9,10-dihydro-9-hydroxy-9-phospha-10-oxaphenanthrene-10-oxide).

In the compounds of the present invention expressed by the general formula (I), it is preferred that at least one of $X_1$ to $X_8$ be an electron-attractive group i.e. halogen, cyano group, acyl group, halogen-substituted alkyl group, halogen-substituted aryl group or aralkyl group, and it is more preferred that at least one of $X_1$ to $X_8$ is halogen. Concrete examples of the substituents are as follows (only substituents at 1 to 8 positions are mentioned as a matter of convenience, and for example, 9,10-dihydro-1-chloro-3-bromo-9-hydroxy-9-phospha- 10-oxaphenanthrene-9-oxide is abbreviated to 1-chloro-3-bromo):

3-fluoro, 6-fluoro, 2,6 difluoro, 1 chloro, 3-chloro, 6-chloro, 1,3-dichloro, 1,3,6-trichloro, 1,3,7-trichloro, 1,3,5,7-tetrachloro, 2,4,6,8-tetrachloro, 3-bromo, 6-bromo, 1,3-dibromo, 2,6-dibromo, 1,3,7-tribromo, 3-cyano, 6-cyano, 1-acetyl, 3-acetyl, 3-benzoyl, 3-trifluoromethyl, 6-trifluoromethyl, 1-phenyl, 3-phenyl, 1-methyl-3-chloro, 1,3,7-trimethyl-6-chloro, 1-methyl-3,7-dichloro, 1,3,7-trimethyl-2,6-dichloro, 1,3,7-trimethyl-6-bromo, 1,3,7-trimethyl-2,6-dibromo, 3-t-butyl-1-chloro, 1-phenyl-3-chloro, 1-phenyl-6-chloro, 1-chloro-3-phenyl, 3-phenyl-1-chloro, 1-(4'-chlorophenyl)-3-chloro, 1-(4'-chlorophenyl)-3,6-dichloro, 1-(4'-chlorophenyl)-3,7-dichloro, 1-benzyl-3-chloro, 3-benzyl-1-chloro, 1-benzyl-3,6-dichloro, 1-chloro-3-bromo, 3-bromo-1-chloro, 1,7-dichloro-3-bromo, 1,3-dibromo-7-chloro or 1,3-dibromo-6-chloro.

Further, if the technical idea of the present invention is appreciated, it will be possible to select further more and feasible combinations of substituents. Any of these cyclic phosphorus compounds from neutral salts together with alkali metals or alkaline earth metals, and any of these salts are in the form of white powder.

Alkali metals referred to herein mean elements belonging to Ia group of the Periodic Table, and as for those which are applicable on a commercial scale, lithium, sodium, potassium and rubidium are mentioned. The flame retardancy and compatibility with substrates, of the flame retardants containing these metals, both increase with the increase in the atomic weight thereof. Alkaline earth metals referred to herein mean elements belonging to IIa group of the Periodic Table, and magnesium, calcium, strontium and barium are mentioned. The flame retardants containing these metals are characterized in that although their flame retardancy and compatibility with substrates are both generally inferior to those in the case of alkali metals excluding lithium in comparison based on the same cyclic phosphorus compounds, they are lower in the water-solubility. Commercially available alkali metals and alkaline earth metals are sodium, potassium, calcium, strontium and barium.

The alkaline earth metal salts of the general formula (I) include those which are compatible with substrates only in an extremely small amount. Attribution of the portion where such salts do not dissolve in substrates, to the flame retardancy, is generally small. However, if even these salts are employed in combination with alkali metal salts of the general formula (I), a tendency that their compatibility is improved is observed. Thus, employment thereof as a mixing salt yields a good result.

Compounds of the general formula (I) and their alkali metal or alkaline earth metal salts which are all novel compounds, can be produced according to various processes.

When alkali metal or alkaline earth metal salts of compounds expressed by the general formula (II)

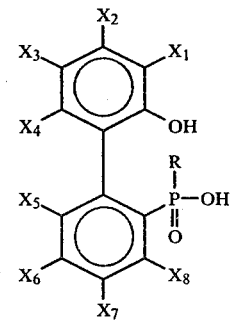

(wherein $X_1$ to $X_8$ have the same definitions as in the general formula (I) (these compounds being produced according to the process disclosed in the specification of U.S. Pat. No. 3,702,878), are heated to 130° C. or higher, they form a ring between —OH and

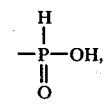

releasing hydrogen atom, resulting in alkali metal or alkaline earth metal salts of the general formula (I). This reaction is smoothly carried out by dissolving or suspending the metal salts in a solvent having a relatively high boiling point such as ethylene glycol, ethylene glycol monoethyl ether, ethylene glycol monobutyl ether, ethylene glycol monophenyl ether, diethylene glycol, diethylene glycol monoethyl ether, propylene glycol, dipropylene glycol, dimethylsulfoxide, dimethylformamide, dichlorobenzene, anisole, phenol or the like. This reaction is a mono-molecular reaction and quantitatively completed. The substituents of $X_1$ to $X_8$ have an influence upon the rate of this reaction. If there is an electron-attractive group among $X_1$ to $X_8$, the reaction rate is reduced. For example, a compound wherein $X_1$ and $X_3$ among $X_1$ to $X_8$ are both chlorine and others are all hydrogen requires higher temperatures by about 30° C. than a compound wherein $X_1$ to $X_8$ are all hydrogen, in order to give the same reaction rate. The reaction temperature is 130° C. or higher, preferably in the range of 150° to 300° C. The reaction is usually completed in one hour to eight hours at a temperature in the range of 180° to 250° C. This mono-molecular reaction is characteristic of those forming cyclic phosphorus compounds as mentioned above, and has an advantage of yielding a product having a high purity with a high yield.

Alternatively, the compounds of the general formula (I) can be obtained by oxidizing phosphorus compounds expressed by the general formula (III)

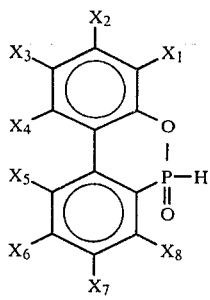

(III)

(wherein $X_1$ to $X_8$ have the same definitions as those of the general formula (I)) (see U.S.Pat. No. 3,702,878). As the oxidizing agent, halogens, hydrogen peroxide and a small amount of potassium iodide, permanganates or chromic acid, etc. can be employed.

Compounds of the general formula (I) or acid halides thereof can be further halogenated with halogens or hypohalides or the like. The positions of halogen substitution vary depending on halogenation method. For example, if bromine is acted on a cyclic phosphorus compound of the general formula (III) wherein $X_1$ to $X_8$ are all hydrogen, in anhydrous state, a vigorous reaction occurs and at first an acid bromide

of the general formula (I) is formed. Further, if an additional molecule of bromine is acted, an acid bromide of the formula (I) wherein $X_3$ is bromine and other Xs are all hydrogen is formed. According to such a manner, halogenation occurs mainly at the positions of the odd numbers. On the other hand, if a cyclic phosphorus compound of the formula (I) wherein $X_1$, $X_3$ and $X_7$ are methyl group and other Xs of $X_1$ to $X_8$ excluding $X_1$, $X_3$ and $X_7$ are all hydrogen is suspended in water, and sodium hypochlorite is added to the resulting suspension at a temperature of 40° C. or lower, followed by stopping the addition when the reaction liquid has become just neutral, then a sodium salt of a cyclic phosphorus compound wherein $X_6$ of the starting cyclic phosphorus compound has turned to chlorine deposits as a crystal. According to such a method, halogenation occurs even at the positions of the even numbers.

The alkali metal salts of the cyclic phosphorus compounds are obtained by neutralizing the compounds of the general formula (I) with an alkali metal hydroxide or an alkali earth metal carbonate. As for the alkaline earth metal salts of the compounds of the general formula (I), since the solubilities of alkaline earth metal salts are low, it is preferable to produce the aforesaid salts by a double decomposition between a water-soluble alkaline earth metal salt and an alkali metal salt of the compounds of the general formula (I). As for the alkali metal salts of the compounds of the general formula (I), if their crystals are deposited from water, this is undesirable since water of crystallization is contained therein. Further, a material having crystals deposited from water is liable to contain a trace of an excessive basic alkali metal compound; hence when used as a flame retardant, it is liable to promote the decomposition of substrates (see Reference example 1 mentioned later). The alkali metal salts of the compounds of the general (I) are most desirable to be purified according to recrystallization method with organic solvents. Flame retardants containing impurities have a great influence upon flame retardancy even when a trace of impurities is present, and there is a fear of leading to an erroneous evalution; hence attention should be paid thereto.

It is presumed that alkali metals or alkaline earth metals play a role of flame retardancy in liquid phase or solid phase at the time of combustion. On the other hand, it is said that halogens which are important as a constituting element of flame retardants effect fire-extinction in gas phase (in flame). Further, among halogens, chlorine and bromine are generally employed as a constituting element of flame retardants.

If other organic halogen compounds are further added to the alkali metal or/and alkaline earth metal salts, in a small amount, a notable increase in the flame retardancy is observed, whereby it is possible to reduce the addition amount flame retardants collectively employed, and hence to minimize the bad effect upon the characteristic properties of substrates, brought about by additives.

As for the organic halogen compounds employable for the object of the present invention, there are mentioned hexachlorobenzene, hexabromobenzene, pentabromotoluene, pentabromochlorocyclohexane, decabromodiphenyl, hexabromodiphenyl ether, decabromodiphenyl ether, perchloropentacyclododecane, tetrabromobisphenol A, polycondensates of tetrabromobisphenol A with carbonic acid, 3,3',5,5'-tetrabromo-4,4'-dioxydiphenyl sulfone, tetrabromophthalic acid esters, hexachloroendomethylene tetrahydrophthalic acid ester, tris (2,3-dibromopropyl) isocyanurate, chlorinated parafins, tris (dichloropropyl) phosphate, tris (2-chloroethyl) phosphate, 9,10-dihydro-1,3-dibromo-9-methyl-9-phospha-10-oxaphenanthrene-9-oxide, dibromophenylglycidyl ether, tribromoglycidyl ether, tribromoaniline, etc. The alkali metal or/and alkaline earth metal salts of the compounds of the general formula (I) may be mixed with organic halogen compounds in any proportion and the resulting mixture may be employed as flame retardants, but preferably 30 to 3,000 parts by weight or organic halogen compounds are mixed with 100 parts by weight of the alkali metal or/and alkaline earth metal salts of the compounds of the general formula (I), and the resulting mixture is added to substrates.

Flame retardants or composite flame retardants according to the present invention exhibit a specific effectiveness upon organic high molecular weight compounds prepared from alkylidenebisphenols as raw material. Such organic high molecular weight compounds include aromatic polycarbonate resins, and resins comprising polycondensates or copolycondensates of aromatic dihydroxyl compounds including alkylidenebisphenols with aromatic dicarboxylic acids, etc. When the flame retardants or composite flame retardants according to the present invention are added in an amount of 0.02 to 10 parts by weight, preferably 0.1 to 5 parts by weight, to 100 parts by weight of substrates comprising these resins, it is possible to obtain resin compositions having a preferable extent of combustibility.

The rating of the flame retarding properties of molding resins such as aromatic polycarbonate resins or polycondensates or copolycondensates of aromatic dihydroxyl compounds with aromatic dicarboxylic acids, is generally carried out according to the standard of Underwriter's Laboratories Inc., Subject 94 (referred to hereinafter as UL-94). According to the flame retardants of the present invention, even when the severest standard of flame retardant properties according to this rating is applied thereto, it is possible to achieve flame retard without any reduction in the characteristic properties of substrates.

In order to make the present invention clearer, it will be explained by way of concrete Examples.

EXAMPLE 1

Into a 2,000 ml capacity 4-neck flask equipped with a reflux condenser having a thermometer, a dropping funnel and a water separator, and a stirrer, are fed 570 g (2mols) of 9,10-dihydro-1,3-dichloro-9-phospha-10-oxaphenanthrene-9-oxide (which corresponds to the general formula (III) and 900 g of ethylene glycol, and a 40% aqueous solution of sodium hydroxide is dropwise added with stirring through the dropping funnel so as to make the pH of the contents nearly neutral with a test paper BTB (Bromthymolblue). Here, sodium salt of a compound corresponding to the general formula (II) is formed. When the flask is then heated, the contents boils to evolve steam. As the steam is removed, the temperature inside the flask rises. When the temperature reaches 170° C., hydrogen begins to evolve. When the temperature is further elevated up to a final one of about 208° C., evolution of hydrogen ceases in about 8 hours. This point is regarded as the end point of reaction. The reaction mixture is poured into 4,000 ml of water. Nearly 10N hydrochloric acid (260 ml) is gradually added to deposit the resulting product as a free acid, which is then cooled down to room temperature, filtered and dried to give about 600 g of crystals, which are, in turn, recrystallized from ethanol to give a white crystalline powder exhibiting a phosphorus content of 10.25% (theoretical value: 10.29%), an acid value of 186 (theoretical value: 186.4), and a melting point of 260° C. or higher (the powder did not melt even when heated up to 260° C.; hence such an expression will be hereinafter employed). It was confirmed according to liquid chromatogram that the powder consisted of a simple substance. It is 9,10-dihydro-1,3-dichloro-9-hydroxy-9-phospha-10-oxaphenanthrene-9-oxide and corresponds to a compound of the general formula (I) wherein $X_1$ and $X_3$ are chlorine and $X_2$, $X_4$, $X_5$, $X_6$, $X_7$ and $X_8$ are all hydrogen. This compound will be hereinafter referred to as CA-Cl, 3.

EXAMPLE 1-1

About 20 g of CA-Cl,3 which is a product in Example 1 are suspended in 100 ml of water contained in a 300 ml capacity beaker. To the resulting suspension is then added a 5% aqueous solution of lithium hydroxide with slow stirring on a water bath, followed by dissolution. The resulting solution is made just neutral, filtered while hot to remove impurities, and concentrated to an extent of concentration to which crystals deposit on slight cooling. The resulting liquid is gradually cooled down to 10° C. to deposit white crystals which are then filtered by a glass filter and dried at 120° C. to give 17 g of crystalline powder. This powder is lithium salt of Ca-Cl,3 and will be hereinafter referred to as CA-Cl,3-Li.

EXAMPLE 1-2

About 20 g of CA-Cl,3 which is a product in Example 1 are suspended in 50 ml of water contained in a 500 ml capacity flask. To the resulting suspension is added a 30% aqueous solution of sodium hydroxide with slow shaking, to dissolve them together and make the resulting liquid just neutral, and further, 300 ml of n-butanol are added. A reflux condenser equipped with a water separator is fixed to the flask, which is then heated to separate water azeotropically. When distilling-off of water has almost ceased, the resulting solution is filtered while hot, and cooled down to 10° C., to deposit white crystals, which are then filtered by a glass filter and dried to give about 19 g crystalline powder. This powder is sodium salt of CA-Cl,3 and will be hereinafter referred to as CA-Cl,3-Na.

EXAMPLE 1-3

About 20 g of CA-Cl,3 are suspended in 20 ml of water contained in a 300 ml capacity flask. To the resulting suspension is added a 40% aqueous solution of potassium hydroxide with shaking of the flask to dissolve them together and make the resulting liquid just neutral, and further, 150 ml of n-butanol are added. A reflux condenser equipped with a water separator is fixed to the flask, which is then heated to separate water azeotropically. When distilling-off of water has almost ceased, the resulting solution is filtered while hot, and cooled down to 10° C., to deposit crystals, which are then filtered by a glass filter and dried to give about 20 g of crystalline powder. This power is potassium salt of CA-Cl,3 and will be hereinafter referred to as CA-Cl,3-K.

EXAMPLE 1-4

About 20 g of CA-Cl,3 are subjected to a neutralization treatment with rubidium carbonate in the same manner as in Example 1-3 to give about 21 g of rubidium salt of CA-Cl,3, which will be hereinafter referred to as CA-Cl,3-Rb.

EXAMPLE 1-5

About 20 g of CA-Cl,3-Na having a high purity, obtained according to the method of Example 1-2 are dissolved in 70 ml of water. The resulting solution is heated up to 70° C., and 30 g of a 20% aqueous solution of magnesium sulfate is added with stirring. After stirring at this temperature for about 20 minutes, the resulting liquid is cooled to deposit precipitate which is then filtered, washed and dried at room temperature to give 18 g of crystalline powder. This powder is magnesium salt of CA-Cl,3 and will be hereinafter referred to as CA-Cl,3-Mg.

EXAMPLE 1-6

About 20 g of CA-Cl,3-Na are dissolved in 100 ml of water and the resulting solution is treated with calcium chloride in the same manner as in Example 1-5 to give about 19 g of calcium salt of CA-Cl,3, which will be hereinafter referred to as CA-Cl,3-Ca.

EXAMPLE 1-7

About 20 g of CA-Cl,3-Na are dissolved in 150 ml of water and the resulting solution is treated with strontium chloride in the same manner as in Example 1-5 to give about 20 g of strontium salt of CA-Cl,3, which will be hereinafter referred to as CA-Cl,3-St.

EXAMPLE 1-8

About 20 g of CA-Cl,3-Na are dissolved in 150 ml of water and the resulting solution is treated with barium chloride in the same manner as in Example 1-5 to give about 20 g of barium salt of CA-Cl,3, which will be hereinafter referred to CA-Cl,3-Ba.

EXAMPLE 2

In the same 4-neck flask as in Example 1 are fed 374 g (1 mol) of 9,10-dihydro-1,3-dibromo-9-phospha-10-oxaphenanthrene-9- oxide and 1,000 g of ethylene glycol, and a 30% aqueous solution of sodium hydroxide is dropwise added with stirring through a dropping funnel, so as to make the contents just neutral with a test paper BTB. Here, sodium salt of a compound of the general formula (II) wherein $X_1$ and $X_3$ are bromine and $X_2$, $X_4$, $X_5$, $X_6$, $X_7$ and $X_8$ are all hydrogen is formed. When the flask is then heated and the temperature of the contents rises, water initially distills off. After separating this water, the temperature of the contents is further elevated so as to exceed 190° C. Here, it is observed that hydrogen is released through the top of the reflux condenser. After about 2 to 3 hours, evolution of hydrogen ceases, and this point is regarded as the end point of reaction. The reaction mixture is poured in 4,000 ml of water. About 10N hydrochloric acid (130 ml) is gradually added and the resulting product is liberated as an acid, followed by sufficient stirring. The resulting liquid is cooled down to 10° C., followed by filtration and drying to give about 370 g of crystals, which are then purified according to recrystallization method with ethylene glycol monomethyl ether to give about 320 g of white crystalline powder exhibiting a phosphorus content of 8.0% (theoretical value: 7.92%), an acid value of 144 (theoretical value: 143.9) and a melting point of 260° C. or higher. It was confirmed according to liquid chromatogram that the powder was a simple substance. It is 9,10-dihydro-1,3-dibromo-9-hydroxy-9-phospha-10-oxaphenanthrene-9-oxide and corresponds to a compound of the general formula (I) wherein $X_1$ and $X_3$ are bromine and $X_2$, $X_4$, $X_5$, $X_6$, $X_7$ and $X_8$ are all hydrogen, which will be hereinafter referred to as CA-Bl,3.

EXAMPLE 2-1

CA-Bl,3 is treated in the same manner as in Examples 1-1 to 1-8 to give the following salts, respectively: lithium salt of CA-Bl,3 (CA-Bl,3-Li), sodium salt of CA-Bl,3 (CA-Bl,3-Na), potassium salt of CA-Bl,3 (CA-Bl,3-K), rubidium salt of CA-Bl,3 (CA-Bl,3-Rb), magnesium salt of CA-Bl,3 (CA-BA,3Mg), strontium salt of CA-Bl,3 (CA-Bl,3-Sr) and barium salt of CA-Bl,3 (CA-Bl,3-Ba).

EXAMPLE 3

Into the same 4-neck flask as in Example 1 are fed 516 g (2 mols) of 9,10-dihydro-3-acetyl-9-phospha-10-oxaphenanthrene-9-oxide and 800 g of diethylene glycol, and a 30% aqueous solution of sodium hydroxide is dropwise added through a dropping funnel with stirring, so as to make the contents just neutral with a test paper BTB. Here, sodium salt of a compound of the general formula (II) wherein $X_3$ is acetyl group and $X_1$ to $X_8$ excluding $X_3$ are all hydrogen is formed. When the flask is then heated and the temperature of the contents rises, water initially distills off and is separated. The temperature of the contents is further elevated so as to exceed 250° C. Here, it is observed that hydrogen is released through the top of the reflux condenser. After about 8 hours, evolution of hydrogen ceases, and this point is regarded as the end point of reaction. The reaction mixture is poured into 4,000 ml of water. About 10N hydrochloric acid (260 ml) is gradually added to liberate the product as an acid. After sufficient stirring, the resulting material is cooled down to 10° C., followed by filtration and drying to give about 500 g of crystals, which are then purified according to recrystallization method from ethanol to give about 420 g of a white crystalline powder exhibiting a phosphorus content of 11.3% (theoretical value: 11.3%), an acid value of 205 (theoretical value: 204.6) and a melting point of 240° C. or higher. It was confirmed according to liquid chromatograph that the power was a simple substance. It is 9,10-dihydro-3-acetyl-9-hydroxy-9-phospha-10-oxaphenanthrene-9-oxide and corresponds to a compound of the general formula (I) wherein $X_3$ is acetyl group and $X_1$ to $X_8$ excluding $X_3$ and all hydrogen, which will be hereinafter referred to as CA-Ac3.

EXAMPLE 3-1

CA-Ac3 is treated in the same manner as in Examples 1-1 to 1-8 to give the following salts, respectively: lithium salt of CA-Ac3(CA-Ac3-Li), sodium salt of CA-Ac3(CA-Ac3-Na), potassium salt of CA-Ac3(CA-Ac3-K), rubidium salt of CA-Ac3(CA-Ac3-Rb), magnesium salt of CA-Ac3(CA-Ac3-Mg), calcium salt of CA-Ac3 (CA-Ac3-Ca), strontium salt of CA-Ac3(A-Ac3-Sr) and barium salt of CA-Ac3(CA-Ac3-Ba).

EXAMPLE 4

9,10-Dihydro-1-chloro-9-phospha-10-oxaphenanthrene-9-oxide (501 g) is treated in the same manner as in Example 1 to give about 420 g of a white powder as a simple substance, of 9,10-dihydro-1-chloro-9-hydroxy-9-phospha-10-oxaphenanthrene-9-oxide exhibiting a phosphorus content of 11.5% (theoretical value: 11.6%), an acid value of 210 (theoretical value: 210.4) and a melting point of 240° C. or higher, which will be hereinafter referred to as CA-Cl.

EXAMPLE 4-1

About 20 g of CA-Cl are suspended in 50 ml of water contained in a 300 ml capacity flask. While the flask is shaked, a 40% aqueous solution of potassium hydroxide is added, to dissolve them together and make the solution just neutral. N-butanol (120 ml) is further added. A reflux condenser equipped with a water separator is fixed to the flask, which is then heated to separate water azeotropically. When distilling-off of water has ceased, the solution is filtered while hot and gradually cooled down to 10° C. White crystals deposit, which are then filtered with a glass filter and dried to give about 20 g of a crystalline powder. This powder is potassium salt of CA-Cl and will be hereiinafter referred to as CA-Cl-K.

EXAMPLE 5

9,10-Dihydro-3-chloro-9-phospha-10-oxaphenanthrene-9-oxide (501 g) is treated in the same manner as in Example 1 to give about 450 g of a white powder as a simple substance, of 9,10-dihydro-3-chloro-9-hydroxy-9-phospha-10-oxaphenanthrene-9-oxide, exhibiting a phosphorus content of 11.9% (theoretical value: 11.6%), an acid value of 211 (theoretical value: 210.4) and a melting point of 240° C. or higher, which will be hereinafter referred to as CA-C3.

EXAMPLE 5-1

About 20 g of CA-C3 are treated in all the same manner as in Example 4-1 to give about 20 g of potassium salt of CA-C3 as white crystal, which will be hereinafter referred to as CA-C3-K.

EXAMPLE 6

Water (300 ml) is fed into a 2,000 ml capacity 4-neck flask equipped with a thermometer, a dropping funnel, a reflux condenser and a stirrer, and 232 g of 9,10-dihydro-9-hydroxy-9-phospha-10-oxaphenanthrene-9-oxide, exhibiting a melting point of 205° C., a phosphorus content of 13.4% (theoretical value: 13.34%) and an acid value of 242 (theoretical value: 241.7) are suspended therein. To the resulting suspension is gradually dropwise added an aqueous solution of sodium hypochlorite having an available chlorine of about 7%, with stirring at room temperature. Since heat generation occurs with the progress of reaction, cooling is carried out so that the temperature of the contents does not exceed 30° C. The aqueous solution of sodium hypochlorite is added till the contents are made just neutral. Although the reaction mixture has already deposited crystals, it is further cooled down to 0° C., followed by filtering and drying the deposited crystals, to give about 190 g of a white powder, which are then dissolved in 1,500 ml of water. An acid is deposited from the resulting solution with about 10 N hydrochloric acid, followed by filtration, drying and recrystallization from ethanol, to give about 140 g of a simple substance exhibiting a phosphorus content of 11.9% (theoretical value: 11.6%), an acid value of 210 (theoretical value: 210.4) and a melting point of 240° C. or higher. This substance is a compound having one chlorine atom, and it was confirmed according to liquid chromatogram and infrared absorption spectra to be the same compound as CA-C3, 9,10-dihydro-3-chloro-9-hydroxy-9-phospha-10-oxaphenanthrene-9-oxide.

EXAMPLE 7

9,10-Dihydro-1,3,7-trimethyl-9-hydroxy-9-phospha-10-oxaphenanthrene-9-oxide (268 g) is treated with an aqueous solution of sodium hypobromite at 60° C. in the same manner as in Example 6, to give about 250 g of 9,10-dihydro-1,3,7-trimethyl-6-bromo-9-hydroxy-9-phospha-10-oxaphenanthrene-9-oxide, exhibiting a phosphorus content of 8.7% (theoretical value: 8.77%), an acid value of 160 (theoretical value: 158,9) and a melting point of 260° C. or higher, which will be hereinafter referred to as CA-M1,3,7-B6.

EXAMPLE 7-1

About 20 g of CA-M1,3,7-B6 are treated in all the same manner as in Example 4-1 to give about 20 g of potassium salt of CA-M1,3,7-B6 as a white crystal, which will be hereinafter referred to as CA-M1,3,7-B6-K.

EXAMPLE 8

CA-M1,3,7-B6 (353 g) is treated with an aqueous solution of sodium hypobromite at 80° C. in the same manner as in Example 6 to give about 320 g of 9,10-dihydro-1,3,7-trimethyl-2,6-dibromo-9-hydroxy-9-phospha-10oxaphenanthrene-9-oxide, exhibiting a phosphorus content of 7.2% (theoretical value: 7.17%), an acid value of 131 (theoretical value: 129.9) and a melting point of 240° C. or higher, which will be hereinafter referred to as CA-M1,3,7-B2,6.

EXAMPLE 8-1

CA-M1,3,7-B2,6 is treated in the same manner as in Examples 1-1 to 1-8 to give the following salts, respectively: lithium salt of CA-M1,3,7-B2,6 (CA-M1,3,7-B2,6-Li), sodium salt of CA-M1,3,7-B2,6 (CA-M1,3,7-B2,6-Na), potassium salt of CA-M1,3,7-B2,6 (CA-M1,3,3,7-B2,6-K), magnesium salt of CA-M1,3,7-B2,6 (CA-M1,3,7-B2,6-Mg), calcium salt of CA-M1,3,7-B2,6 (CA-M1,3,7-B2,6-Ca), strontium salt of CA-M1,3,7-B2,6 (CA-M1,3,7-B2,6Sr) and barium salt of CA-M1,3,7-B2,6 (CA-M1,3,7-B2,6-Ba).

EXAMPLE 9

Into a 200 ml capacity 3-neck flask equipped with a thermometer, a reflux condenser and a stirrer are fed 50 g of potassium salt of 9,10-dihydro-6-bromo-9-hydroxy-9-phospha-10-oxaphenanthrene-9-oxide (CA-B6-K), 30 g of potassium fluoride and 100 g of diethylene glycol, and the flask is heated with stirring so that the contents boil slowly. Dioxane and water are formed little by little to reduce the temperature of the contents. Thus, while they are taken out, the initial boiling temperature is maintained to carry out the reaction for 8 hours. The reaction mixture is cooled down to room temperature to deposit an excess amount of potassium fluoride and potassium bromide formed by the reaction, which are then filtered off. To the resulting filtrate are added 100 ml of water and thereafter 30 ml of 10 N hydrochloric acid to deposit an acid, which is then filtered, dried and recrystallized from ethanol to give about 20 g of 9,10-dihydro-6-fluoro-9-hydroxy-9-phospha-10-oxaphenanthrene-9-oxide, exhibiting a phosphorus content of 12.3% (theoretical value: 12.4%), an acid value of 224 (theoretical value: 224.3) and a melting point of 240° C. or higher, which will be hereinafter referred to as CA-F6.

EXAMPLE 9-1

About 20 g of CA-F6 are treated in all the same manner as in Example 4-1 to give about 21 g of potassium salt of CA-F6 as a white crystal, which will be hereinafter referred to as CA-F6-K.

EXAMPLE 10

Into the same 3-neck flask as in Example 9 are fed 50 g of CA-B6-K, 30 g of potassium cyanide and 100 g of diethylene glycol, and the flask is then heated with stirring so that the contents boil slowly. Dioxane and water are formed to reduce the boiling point. Thus, while they are taken out, the initial boiling temperature is maintained to carry out the reaction for 5 hours. Water (150 ml) is added to the reaction mixture, and further, 10 N hydrochloric acid is added till no more crystal deposits. Since hydrogen cyanide, a deadly poison, evolves at the same time, hydrochloric acid must be added paying attention so as not to inhale it. The crystals which deposited are filtered, dried and recrystallized from ethanol to give about 26 g of 9,10-dihydro-6-cyano-9-hydroxy-9-phospha-10-oxaphenanthrene-9-oxide, exhibiting a phosphorus content of 12% (theoretical value: 12.04%), an acid value of 220 (theoretical value: 218.2) and a melting point of 240° C. or higher, which will be hereinafter referred to as CA-CN6.

EXAMPLE 10-1

About 20 g of CA-CN6 are treated in the same manner as in Example 4-1 to give about 20 g of potassium salt of CA-CN6 as a white crystal, which will be hereinafter referred to as CA-CN6-K.

EXAMPLE 11

About 30 g of CA-CN6 are treated with boron trifluoride to give about 20 g, of 9,10-dihydro-6-trifluoromethyl-9-hydroxy-9-phospha-10-oxaphenanthrene-9-oxide, exhibiting a phosphorus content of 10.1% (theoretical value: 10.3%), an acid value of 188 (theoretical value: 186.9) and a melting point of 240° C. or higher, which will be hereinafter referred to as CA-TFM6.

EXAMPLE 11-1

About 20 g CA-TFM6 are treated in all the same as in Example 4-1 to give about 20 g of potassium salt of CA-TFM6 as a white crystal, which will be hereinafter referred to as CA-TFM6-K.

EXAMPLE 12

9,10-Dihydro-1,3,7-trichloro-9-phospha-10-oxaphenanthrene-9-oxide (384 g) is treated in the same manner as in Example 3 to give 320 g of 9,10-dihydro-1,3,7-trichloro-9-hydroxy-9-phospha-10-oxaphenanthrene-9-oxide, exhibiting a phosphorus content of 9.1% (theoretical value: 9.23%), an acid value of 168.7 (theoretical value: 167.22) and a melting point of 260° C. or higher, which will be hereinafter referred to as CA-C1,3,7.

EXAMPLE 12-1

CA-C1,3,7 is treated in the same manner as in Examples 1—1 to 1-8 to give the following salts, respectively: lithium salt of CA-C1,3,7 (CA-C1,3;7-Li), sodium salt of CA-C1,3,7 (CA-C1,3,7-Na), potassium salt of CA-C1,3,7 (CA-C1,3,7-K), rubidium salt of CA-C1,3,7 (CA-C1,3,7-Rb), magnesium salt of CA-C1,3,7 (CA-C1,3,7-Mg), calcium salt of CA-C1,3,7 (CA-C1,3,7-Ca), strontium salt of CA-C1,3,7 (CA-C1,3,7-Sr) and barium salt of CA-C1,3,7 (CA-C1,3,7-Ba).

EXAMPLE 13

9,10-Dihydro-3-t-butyl-9-hydroxy-9-phospha-10-oxaphenanthrene-9-oxide (288 g) is treated in the same manner as in Example 6 to give 280 g of 9,10-dihydro-3-t-butyl-1-chloro-9-hydroxy-9-phospha-10-oxaphenanthrene-9-oxide, exhibiting a phosphorus content of 9.5% (theoretical value: 9.60%), an acid value of 174 (theoretical value: 173.8) and a melting point of 240° C. or higher, which will be hereinafter referred to as CA-Bu3-Cl.

EXAMPLE 13-1

About 20 g of CA-Bu3-Cl are treated in all the same as in Example 4-1 to give about 20 g of potassium salt of CA-Bu3-Cl as a white crystal, which will be hereinafter referred to as CA-Bu3-Cl-K.

EXAMPLE 14

9,10-Dihydro-1-(4'-chlorophenyl)-3,7-dichloro-9-phospha-10-oxaphenanthrene-9-oxide (495.5 g) is treated in the same manner as in Example 3 to give 460 g of 9,10-dihydro-1-(4'-chlorophenyl)-3,7-dichloro-9-hydroxy-9-phospha-10-oxaphenanthrene-9-oxide, exhibiting a phosphorus content of 7.7% (theoretical value: 7.53%), an acid value of 140 (theoretical value: 136.3) and a melting point of 260° C. or higher, which will be hereinafter referred to as CA-CP1-C3,7.

EXAMPLE 14-1

About 20 g of CA-CP1-C3,7 are treated in all the same as in Example 4-1 to give about 20 g of potassium salt of CA-CP1-C3,7 as a white crystal, which will be hereinafter referred to as C3,7-K.

EXAMPLE 15

9,10-Dihydro-1-phenyl-9-hydroxy-9-phospha-10-oxaphenantrene-9-oxide (308 g) is treated in all the same as in Example 6 to give 250 g of 9,10-dihydro-1-phenyl-3-chloro-9-hydroxy-9-phospha-10-oxaphenanthrene-9-oxide, exhibiting a phosphorus content of 9.1% (theoretical value: 9.04%), an acid value of 165 (theoretical value: 163.7) and a melting point of 260° C. or higher, which will be hereinafter referred to as CA-P1-C3.

EXAMPLE 15-1

About 20 g of CA-P1-C3 are treated in all the same as in Example 4-1 to give about 20 g of potassium salt of CA-P1-C3 as a white crystal, which will be hereinafter referred to as CA-P1-C3-K.

EXAMPLE 16

9,10-Dihydro-3-benzyl-9-hydroxy-9-phospha-10-oxaphenanthrene-9-oxide (322 g) is treated in all the same as in Example 6 to give 270 g of 9,10-dihydro-3-benzyl-1-chloro-9-hydroxy-9-phospha-10-oxaphenanthrene-9-oxide, exhibiting a phosphorus content of 8.6% (theoretical value: 8.68%), an acid value of 160 (theoretical value: 157.3) and a melting point of 240° C. or higher, which will be hereinafter referred to as CA-Bz3-Cl.

EXAMPLE 16-1

About 20 g of CA-Bz3-Cl are treated in all the same as in Example 4-1 to give about 20 g of potassium salt of CA-Bz3-Cl as a white crystal, which will be hereinafter referred to as CA-Bz3-Cl-K.

EXAMPLE 17

Flame retardants are added to 100 parts by weight of Panlite K-1,300 (tradename of a polycarbonate resin which is a polycondensate of bisphenol A with carbonic acid, manufactured by Teijin Kasei Kabushiki Kaisha, Japan), and the resulting mixture is kneaded at 270° C. by a Brabender mill for laboratories. The resulting material is molded by a compression molding machine at 280° C. to prepare a sheet of 1.5 mm thick, from which a test piece having a length of 127 mm and a width of 13 mm is cut off. This test piece is subjected to evaluation and rating of flame retardant properties according to the testing method of UL94. The rating is classified into 4 stages of HB, V-2, V-1 and V-0, and judgment is so made that the later stage in the above order is superior in the flame retardant properties.

EXAMPLE 17-1

The flame retardant properties of products obtained in Examples 1-1 to 1-8 were tested according to Example 17. The results are shown in Table 1. The difference in the effectiveness between alkali metal salts and alkaline earth metal salts will be understood from this Table.

TABLE 1

| Flame retardant | Amount added (part) | Rating | Amount added (part) | Rating |
|---|---|---|---|---|
| None | — | HB | | |

TABLE 1-continued

| Flame retardant | Amount added (part) | Rating | Amount added (part) | Rating |
|---|---|---|---|---|
| CA-C1,3-Li | 0.5 | V-2 | 2.0 | V-1 |
| CA-C1,3-Na | 0.5 | V-1 | 2.0 | V-0 |
| CA-C1,3-K | 0.5 | V-1 | 2.0 | V-0 |
| CA-C1,3-Rb | 0.5 | V-1 | 2.0 | V-0 |
| CA-C1,3-Mg | 0.5 | V-2 | 2.0 | V-2 |
| CA-C1,3-Ca | 0.5 | V-2 | 2.0 | V-1 |
| CA-C1,3-Sr | 0.5 | V-1 | 2.0 | V-1 |
| CA-C1,3-Ba | 0.5 | V-1 | 2.0 | V-1 |

EXAMPLE 17-2

The flame retardant properties of the products obtained in Examples 2-1, 3-1, 8-1 and 12-1 were tested according to Example 17. The results are shown in Table 2.

TABLE 2

| Flame retardant | Amount added (part) | Rating | Transparency |
|---|---|---|---|
| CA-B1,3-Li | 2.0 | HB | transparent |
| CA-B1,3-Na | 2.0 | V-2 | transparent |
| CA-B1,3-K | 2.0 | V-2 | transparent |
| CA-B1,3-Rb | 2.0 | V-1 | transparent |
| CA-B1,3-Mg | 2.0 | HB | a little turbid |
| CA-B1,3-Ca | 2.0 | V-2 | turbid |
| CA-B1,3-Sr | 2.0 | V-2 | turbid |
| CA-B1,3-Ba | 2.0 | V-2 | turbid |
| CA-Ac3-Li | 2.0 | V-1 | transparent |
| CA-Ac3-Na | 2.0 | V-0 | transparent |
| CA-Ac3-K | 2.0 | V-0 | transparent |
| CA-Ac3-Rb | 2.0 | V-0 | transparent |
| CA-Ac3-Mg | 2.0 | V-1 | turbid |
| CA-Ac3-Ca | 2.0 | V-1 | turbid |
| CA-Ac3-Sr | 2.0 | V-0 | turbid |
| CA-Ac3-Ba | 2.0 | V-0 | turbid |
| CA-M1,3,7-B2,6-Li | 2.0 | V-0 | transparent |
| CA-M1,3,7-B2,6-Na | 2.0 | V-0 | transparent |
| CA-M1,3,7-B2,6-K | 2.0 | V-0 | transparent |
| CA-M1,3,7-B2,6-Rb | 2.0 | V-0 | transparent |
| CA-M1,3,7-B2,6-Mg | 2.0 | V-1 | a little turbid |
| CA-M1,3,7-B2,6-Ca | 2.0 | V-0 | turbid |
| CA-M1,3,7-B2,6-Sr | 2.0 | V-0 | turbid |
| CA-M1,3,7-B2,6-Ba | 2.0 | V-0 | turbid |
| CA-C1,3,7-Li | 2.0 | V-1 | transparent |
| CA-C1,3,7-Na | 2.0 | V-0 | transparent |
| CA-C1,3,7-K | 2.0 | V-0 | transparent |
| CA-C1,3,7-Rb | 2.0 | V-0 | transparent |
| CA-C1,3,7-Mg | 2.0 | V-1 | a little turbid |
| CA-C1,3,7-Ca | 2.0 | V-0 | turbid |
| CA-C1,3,7-Sr | 2.0 | V-0 | turbid |
| CA-C1,3,7-Ba | 2.0 | V-0 | turbid |

Among the alkaline earth metal salts in Table 2, those having an inferior compatibility are observed, but their compatibilities are improved by the simultaneous use thereof with the alkali metal salts. For example, when 1.0 part of the above mentioned CA-M1,3,7-B2,6-K is blended with 1.0 part of the above-mentioned CA-M1,3,7-B2,6-Ca, flame retardant which is transparent and yet has a rating of V-0 is obtained.

EXAMPLE 17-3

With compounds selected from among those of the respective Examples, tests of flame retardant properties through which the difference in the effect of halogen and the difference in the effect due to the position of substitution were carried out according to Example 17. The results are shown in Table 3.

TABLE 3

| Flame retardant | Amount added (part) | Rating | Transparency |
|---|---|---|---|
| CA-C1-K | 2.0 | V-2 | transparent |
| CA-C3-K | 2.0 | V-2 | transparent |
| CA-B1,3-K | 2.0 | V-2 | transparent |
| CA-M1,3,7-B2,6-K | 2.0 | V-0 | transparent |
| CA-M1,3,7-B6-K | 2.0 | V-1 | transparent |
| CA-F6-K | 2.0 | V-0 | a little turbid |

EXAMPLE 17-4

With compounds of other Examples, evaluation of flame retardant properties was carried out according to Example 17. The results are summarized in Table 4.

TABLE 4

| Flame retardant | Amount added (part) | Rating | Transparency |
|---|---|---|---|
| CA-CN6-K | 2.0 | V-0 | a little turbed |
| CA-TFM6-K | 2.0 | V-0 | transparent |
| CA-Bu3-C1-K | 2.0 | V-1 | transparent |
| CA-CP1-C3,7-K | 2.0 | V-0 | transparent |
| CA-P1-C3-K | 2.0 | V-1 | transparent |
| CA-Bz3-C1-K | 2.0 | V-1 | transparent |

EXAMPLE 18

A flame retardant and organic halogen compounds (halides) are added to 100 parts by weight of Panlite K1-1,300 (an aromatic polycarbonate resin which is a polycondensate of bisphenol A with carbonic acid) and the flame retardant properties of the resulting compositions are evaluated and rated according to Example 17. The results are shown in Table 5. The compositions were all transparent. (The amount added is expressed by part by weight.)

TABLE 5

| Flame retardant | Amount added | Halide | Amount added | Rating |
|---|---|---|---|---|
| — | — | DBDE[1] | 2.0 | HB |
| — | — | TBA[2] | 2.0 | HB |
| — | — | BPC[3] | 2.0 | HB |
| CA-C1,3-K | 0.5 | DBDE | 0.5 | V-0 |
| CA-C1,3-Rb | 0.3 | BPC | 1.0 | V-0 |
| CA-Ac3-K | 0.5 | DBDE | 1.0 | V-0 |
| CA-C1,3,7-K | 0.2 | DBDE | 0.5 | V-0 |
| CA-C1-K | 2.0 | DBDE | 2.0 | V-0 |
| CA-C3-K | 2.0 | DBDE | 2.0 | V-1 |
| CA-B1,3-K | 2.0 | DBDE | 2.0 | V-1 |
| CA-M1,3,7-B2,6-K | 0.5 | DBDE | 1.0 | V-0 |
| CA-M1,3,7-B6-K | 1.0 | DBDE | 2.0 | V-0 |
| CA-F6-K | 0.1 | DBDE | 0.5 | V-0 |
| CA-CN6-K | 0.5 | DBDE | 0.5 | V-0 |
| CA-TFM6-K | 0.5 | DBDE | 0.5 | V-0 |
| CA-Bu3-C1-K | 0.5 | DBDE | 1.0 | V-1 |
| CA-CP1-C3,7-K | 0.5 | DBDE | 1.0 | V-0 |
| CA-P1-C3-K | 0.5 | DBDE | 1.0 | V-1 |
| CA-BZ3-C1-K | 0.5 | DBDE | 1.0 | V-1 |

[1]: Decabromodiphenyl ether
[2]: Tetrabromobisphenol A
[3]: Polycondensate of tetrabisphenol A with carbonic acid

EXAMPLE 19

A flame retardant or a composite flame retardant is added to 100 parts by weight of a resin which is a copolycondensate of bisphenol A with terephthalic acid and isophthalic acid and has an average of repetition units of bisphenol A of 70, followed by kneading by a Brabender mill for laboratories at 290° C., and then molding by a compression molding machine at 300°, to prepare a sheet of 1.5 mm thick, from which a test piece having a length of 127 mm and a width of 13 mm is then cut off and subjected to evaluation of flame retardant properties in the same manner as in Example 17. The results are shown in Table 6. The resulting compositions were all transparent. (The amount added is expressed by part by weight.)

TABLE 6

| Flame retardant | Amount added | Halide | Amount added | Rating |
|---|---|---|---|---|
| None | — | None | — | HB |
|  |  | DBDE | 2.0 | HB |
| CA-Cl,3,7-K | 2.0 | None | — | V-1 |
| CA-Cl,3,7-K | 1.0 | DBDE | 1.0 | V-0 |
| CA-Cl,3-K | 1.0 | DBDE | 1.0 | V-0 |
| CA-Ml,3,7-B2,6-K | 1.0 | DBDE | 1.0 | V-0 |
| CA-C3-K | 1.0 | DBDE | 1.0 | V-0 |
| CA-Pl-C3-K | 1.0 | DBDE | 1.0 | V-0 |
| CA-Ac-3-K | 1.0 | BPC | 1.0 | V-0 |

REFERENCE EXAMPLE 1

As for the flame retardants of the present invention, when they are applied particularly to aromatic polycarbonate resins, impurities may harm the characteristic properties of substrates. Next, one example thereof will be illustrated. About 20 g of CA-B1,3 which is the product of Example 2 and 50 ml of water are fed into a 100 ml beaker, and a 20% aqueous solution of potassium hydroxide is added with slow stirring on a water bath so that the liquid becomes just neutral with a test paper of BTB. The resulting liquid is then concentrated to such an extent of concentration that crystals deposit when it is a little cooled, followed by cooling to deposit crystals, which are then filtered and collected. Since the crystals contain water of crystallization, they are dried at 120° C. to give a white powder. This powder corresponds to CA-B1,3-K according to Example 2-1, but when a material obtained by adding only 0.1 part by weight of it to 100 parts by weight of an aromatic polycarbonate resin is evaluated according to claim 17, a rating of V-0 is given, whereas when 0.1 part by weight of it is added to 100 parts by weight of an aromatic polycarbonate resin having an average molecular weight of 23,000 and the resulting material is maintained at 320° C. for 5 minutes, the average molecular weight lowers down to 6,000. On the other hand, in Example 17 and Example 18, any of the test pieces employed maintained the molecular weights of the original resins, that is, no reduction in the molecular weight was observed.

We claim:

1. A flame retardant comprising alkali metal and/or alkaline earth metal salts of a cyclic phosphorus compound represented by formula I,

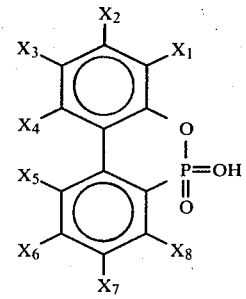

wherein each of $X_1$ to $X_8$ represents hydrogen, halogen, cyano, acyl, alkyl, halogen-substituted alkyl, aryl, halogen-substituted aryl or aralkyl.

2. The flame retardant of claim 1 wherein at least one of $X_1$ to $X_8$ is an electron attractive group selected from the group consisting of halogen, cyano, acyl, halogen-substituted alkyl, aryl and halogen-substituted aryl.

3. The flame retardant of claim 2 wherein the electron attractive group is halogen.

4. The flame retardant of claim 1 wherein $X_1$ and $X_3$ are both halogen and $X_2$ and $X_4$ to $X_8$ are all hydrogen.

5. A composite flame retardant comprising a mixture of 100 parts by weight of alkali metal and/or alkaline earth metal salts of a cyclic phosphorus compound represented by the formula I of claim 1 and 30 to 3,000 parts by weight of an organohalogen compound.

6. A flame retardant resin composition comprising 100 parts by weight of a substrate selected from the group consisting of an aromatic polycarbonate resin and a polycondensate or copolycondensate of an aromatic dihydroxyl compound with an aromatic dicarboxylic acid, 0.02 to 5 parts by weight of alkali metal and/or alkaline earth metal salts of a cyclic phosphorus compound represented by the formula I of claim 1 and 0 to 5 parts by weight of an organohalogen compound.

7. A process for preparing alkali metal and/or alkaline earth metal salts of a cyclic phosphorus compound represented by the formula I, of claim 1 which comprises dehydrogenizing alkali metal and/or alkaline earth metal salts of a phosphorus compound represented by formula II,

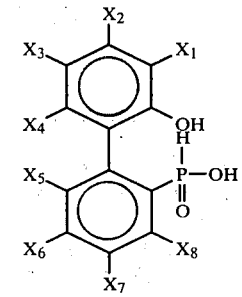

wherein each of $X_1$ to $X_8$ is as defined in the formula I under heating at temperatures above 130° C.

* * * * *